United States Patent
Yonehara et al.

(10) Patent No.: US 11,525,931 B2
(45) Date of Patent: Dec. 13, 2022

(54) GAS-FILLED RADIO-FREQUENCY BEAM DETECTOR

(71) Applicant: Muons, Inc., Batavia, IL (US)

(72) Inventors: Katsuya Yonehara, Geneva, IL (US); Rolland Paul Johnson, Newport News, VA (US); Grigory Kazakevich, North Aurora, IL (US); Alfred Moretti, Berwin, IL (US)

(73) Assignee: Muons, Inc., Batavia, IL (US)

( * ) Notice: Subject to any disclaimer, the term of this patent is extended or adjusted under 35 U.S.C. 154(b) by 309 days.

(21) Appl. No.: 16/855,125

(22) Filed: Apr. 22, 2020

(65) Prior Publication Data

US 2020/0333480 A1    Oct. 22, 2020

Related U.S. Application Data

(60) Provisional application No. 62/836,767, filed on Apr. 22, 2019.

(51) Int. Cl.
*G01T 1/26* (2006.01)
*H05H 7/02* (2006.01)
*H05H 7/12* (2006.01)

(52) U.S. Cl.
CPC ............ *G01T 1/26* (2013.01); *H05H 7/02* (2013.01); *H05H 2007/122* (2013.01)

(58) Field of Classification Search
None
See application file for complete search history.

(56) References Cited

U.S. PATENT DOCUMENTS

| | | | | |
|---|---|---|---|---|
| 3,239,664 A | * | 3/1966 | Farrell | G01T 1/28 250/389 |
| 3,496,463 A | * | 2/1970 | Johnston | H01J 29/54 250/336.1 |
| 3,733,546 A | * | 5/1973 | Faltens | G01T 1/29 250/492.1 |
| 4,357,536 A | * | 11/1982 | Varma | G01T 1/29 250/397 |
| 4,494,040 A | * | 1/1985 | Moretti | H01J 23/20 315/505 |
| 4,724,321 A | * | 2/1988 | Edlin | G01T 1/16 250/336.1 |

(Continued)

OTHER PUBLICATIONS

"G4Beamline", © Muons, Inc. [online]. Retrieved from the Internet: <URL: http://public.muonsinc.com/Projects/G4beamline.aspx>, (2020), 3 pgs.

(Continued)

*Primary Examiner* — Srinivas Sathiraju
(74) *Attorney, Agent, or Firm* — Schwegman Lundberg & Woessner, P.A.

(57) ABSTRACT

A system for monitoring intensity of a particle beam can include one or more radio-frequency (RF) detectors coupled to a signal analyzer that can be placed outside the radiation field of the particle beam. Each RF detector can include a gas-filled RF cavity coupled to one or more gas-filled waveguides. The signal analyzer can self-calibrate before the particle beam is turned on for determining one or more absolute intensities of the particle beam when the particle beam is present.

20 Claims, 7 Drawing Sheets

(56) References Cited

U.S. PATENT DOCUMENTS

| | | | | |
|---|---|---|---|---|
| 4,877,961 | A * | 10/1989 | McIntyre | H05H 7/00 |
| | | | | 313/363.1 |
| 5,773,833 | A * | 6/1998 | Hsi | G01N 27/64 |
| | | | | 250/382 |
| 9,726,768 | B2 * | 8/2017 | Friedman | G01T 1/26 |
| 10,367,508 | B1 * | 7/2019 | Miller | H05H 9/047 |
| 2003/0128554 | A1 * | 7/2003 | Crewson | H02M 3/33573 |
| | | | | 363/16 |
| 2010/0001231 | A1 * | 1/2010 | Loukus | C04B 41/009 |
| | | | | 249/105 |
| 2010/0265078 | A1 * | 10/2010 | Friedman | G01T 1/26 |
| | | | | 340/600 |
| 2012/0227624 | A1 * | 9/2012 | Loukus | C04B 41/88 |
| | | | | 249/105 |
| 2013/0068956 | A1 * | 3/2013 | Friedman | G01T 1/26 |
| | | | | 250/382 |
| 2014/0318489 | A1 * | 10/2014 | Ben-Haim | F23C 99/001 |
| | | | | 123/143 R |
| 2017/0265292 | A1 * | 9/2017 | Mishin | H05H 9/02 |
| 2017/0322326 | A1 * | 11/2017 | Friedman | H01J 47/08 |
| 2018/0374588 | A1 * | 12/2018 | Johnson | B01D 5/0036 |
| 2020/0333480 | A1 * | 10/2020 | Yonehara | H05H 7/02 |
| 2020/0395137 | A1 * | 12/2020 | Heibel | G01T 1/24 |
| 2021/0353966 | A1 * | 11/2021 | Michaud | G21K 1/093 |

OTHER PUBLICATIONS

"Long-Baseline Neutrino Experiment (LBNE) Project Conceptual Design Report, vol. 2: The Beamline at the Near Site", [online]. Retrieved from the Internet: <URL: https://radiate.fnal.gov/downloads/LBNE_CDR_Vol2-101812.pdf>, (Oct. 2012), 211 pgs.

Chase, B., et al., "Precision vector control of a superconducting RF cavity driven by an injection locked magnetron", 2015 Journal of Instrumentation 10 P03007, (2015), 14 pgs.

Chung, M., et al., "Pressurized $H_2$ RF Cavities in Ionizing Beams and Magnetic Fields", FERMILAB-PUB-13-269-APC, (2013), 1-5.

Freemire, B., et al., "Plasma Chenistry in a High Pressure Gas Filled RF Test Cell for Use in a Muon Cooling Channel", Proceedings of 5th International Particle Accelerator Conference (IPAC 2014), (2014), 3917-3920.

Johnson, R. P., "Final Technical Report on STTR Project DE-FG02-02ER86145 Pressurized RF Cavities for Muon Ionization Cooling", Report No. DOE/ER-86145-F, Muons, Inc., (2006), 1-83.

Yonehara, K., et al., "Gas Filled RF Resonator Hadron Beam Monitor for Intense Neutrino Beam Experiments", Proceedings of IPAC2016, Busan, Korea, (2016), 2733-2735.

Yonehara, K., et al., "New Hadron Monitor by Using a Gas-Filled RF Resonator", Proceedings of 6th International Particle Accelerator Conference (IPAC 2015), (2015), 1189-1191.

Yonehara, K., et al., "Progress of Gas-Filled Multi-RF-Cavity Beam Profile Monitor for Intense Neutrino Beams", Proceedings of NAPAC2016, Chicago, IL, USA, (2016), 1275-1278.

Yonehara, K., et al., "Summary of Dense Hydrogen Gas Filled RF Cavity Test for Muon Acceleration", Proceedings of IPAC2013, Shanghai, China, TUPFI059, (2013), 1481-1483.

Zwaska, R., et al., "Beam Tests of Ionization Chambers for the NuMI Neutrino Beam", IEEE Trans. Nucl. Sci. 50(4), (Aug. 2003), 1129-1135.

Zwaska, R. M., et al., "Operation of the NuMI Beam Monitoring System", AIP Conference Proceeding, CP868, Beam Instrumentation Workshop, (2006), 558-565.

* cited by examiner

A: OBSERVED SPECTRUM OF THE RF DETECTOR
B: GAUSSION FIT OF A
C: OBSERVED POWER OF THE FORWARD RF SIGNAL
D: OBSERVED POWER OF THE REFLECTED RF SIGNAL

GAS-FILLED RADIO-FREQUENCY BEAM DETECTOR

CLAIM OF PRIORITY

This application claims the benefit of priority under 35 U.S.C. § 119(e) of U.S. Provisional Patent Application Ser. No. 62/836,767, entitled "ELECTRONICS OF GAS-FILLED RADIO-FREQUENCY BEAM DETECTOR", filed on Apr. 22, 2019, which is herein incorporated by reference in its entirety.

GOVERNMENT SUPPORT

This invention was made with government support under Grant No. DE-SC0013795 awarded by the United States Department of Energy STTR Office. The United States Government has certain rights in the invention.

TECHNICAL FIELD

This document relates generally to particle accelerators and more particularly, but not by way of limitation, a gas-filled radio-frequency (RF) beam detector for measuring beam intensity in radiation environment for a beam facility.

BACKGROUND

One of the biggest challenges in the modern accelerator physics is building a megawatt (MW)-class beam facility. Such a facility may produce secondary and tertiary particles by hitting a primary beam on a target to study fundamental particle physics or apply for a subcritical nuclear reactor. A radiation-hard beam detector is an essential beam element to maintain the quality of the primary and secondary beams. A currently used beam detector has issues including limited lifetime, and hence high cost associated with frequent replacement, and need for handling irradiated detector waste.

SUMMARY

A system for monitoring intensity of a particle beam can include one or more radio-frequency (RF) detectors coupled to a signal analyzer that can be placed outside the radiation field of the particle beam. Each RF detector can include a gas-filled RF cavity coupled to one or more gas-filled waveguides. The signal analyzer can self-calibrate before the particle beam is turned on for determining one or more absolute intensities of the particle beam when the particle beam is present.

In one embodiment, an apparatus for monitoring intensity of a particle beam inside a radiation enclosure can include one or more RF detectors and a signal analyzer. The one or more RF detectors can each include a gas-filled RF cavity and one or more gas-filled waveguides. The gas-filled RF cavity can be configured to be placed inside the radiation enclosure. The one or more gas-filled waveguides are coupled to the gas-filled RF cavity for transmitting a forward RF signal to the gas-filled RF cavity and a returning RF signal from the gas-filled RF cavity. The signal analyzer can be configured to be placed outside of the radiation enclosure, and can be coupled to the one or more gas-filled waveguides of each RF detector of the one or more RF detectors to receive the forward and returning RF signals, to self-calibrate without presence of the particle beam for determining one or more absolute intensities of the particle beam using the received forward and returning RF signals, and to determine the one or more absolute intensities of the particle beam using the received forward and returning RF signals when the particle beam is present after the self-calibration.

In one embodiment, a method for monitoring intensity of a particle beam inside a radiation enclosure is provided. The method can include placing one or more radio-frequency (RF) cavities in a path of the particle beam inside the radiation enclosure, transmitting a forward RF signal to each RF cavity of the one or more RF cavities and a returning RF signal from that RF cavity through one or more gas-filled waveguides coupled to that RF cavity, receiving the forward and returning RF signals using a signal analyzer placed outside the radiation enclosure and coupled to the one or more waveguides coupled to each RF cavity of the one or more RF cavities, performing self-calibration for each RF cavity of the one or more RF detectors without presence of the particle beam for determining one or more absolute intensities of the particle beam using the received forward and returning RF signals, and determining the one or more absolute intensities of the particle beam using the received forward and returning RF signals when the particle beam is present after the self-calibration.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a system and method for monitoring intensity of a particle beam in a radiation enclosure using a signal analyzer that can be placed outside of the radiation enclosure and can self-calibrate without the presence of the particle beam. According to the present subject matter, a gas-filled RF beam detector has been developed to overcome issues associated with existing beam detector, such as high cost associated with need for frequent replacement and handling irradiated detector waste. The present detector is constructed of metal to significantly improve its life expectancy. The RF signal can be analyzed outside the radiation enclosure so that problems (e.g., varying gain) associating with device aging are addressed.

Figure 1:
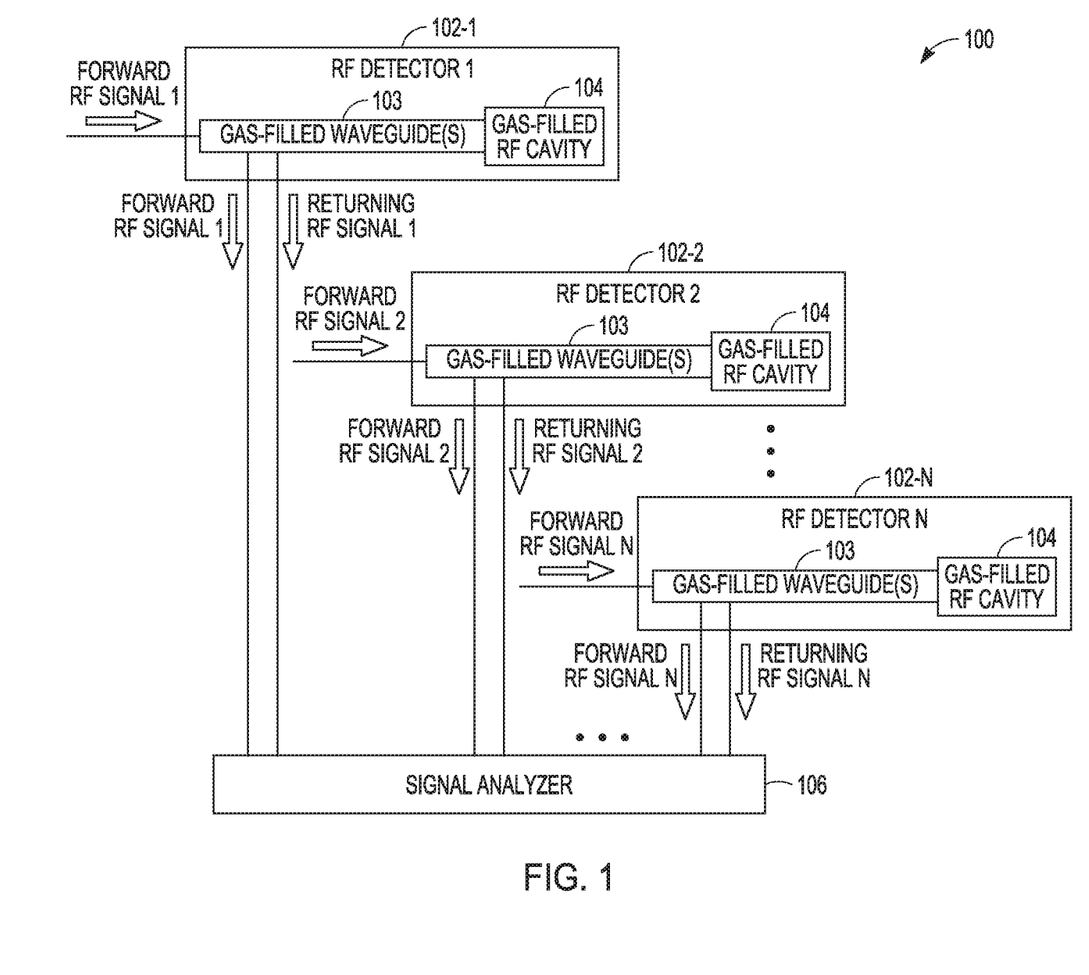
FIG. 1 illustrates an embodiment of an RF beam intensity detector including one or more RF detectors and a signal analyzer.

FIG. 1 illustrates an embodiment of an RF beam intensity detector 100 including one or more RF detectors 102 and a signal analyzer 106. Detector 100 can be used for monitoring intensity of a particle beam inside a radiation enclosure. RF detector(s) 102 each include one or more gas-filled waveguides 103 and a gas-filled RF cavity (also referred to as RF resonator) 104. RF cavity 104 can be placed inside the radiation enclosure. Waveguide(s) 103 can be used to transmit a forward RF signal to RF cavity 104 and a returning RF signal from RF cavity 104. Signal analyzer 106 can be placed outside of the radiation enclosure and coupled to waveguide(s) 103 of each of RF detector(s) 102 to receive the forward and returning RF signals. Signal analyzer 106 can self-calibrate without presence of the particle beam for determining one or more absolute intensities of the particle beam using the received forward and returning RF signals, and can then determine the one or more absolute intensities of the particle beam using the received forward and returning RF signals when the particle beam is present after the self-calibration.

In this document, an "absolute intensity" includes a measure of an actual intensity, rather than, for example, a measure of a change of an intensity or a measure of intensity that is referenced to another parameter. A "self-calibration" as discussed in this document can include self-calibration for establishing a baseline for RF power measurements for each RF detector when the particle beam is not present such that absolute intensities can be determined for that RF detector using the RF power measurements with the particle beam being present. For the self-calibration, a shunt impedance (Z) is a characteristic of detector 100 that can be determined for each of RF detector 102 using signal analyzer 106, without presence of the particle beam, by sending an RF signal with a calibrated current through each of RF detector 102 and measuring the change in voltage. The absolute beam intensity can be calculated from the current (I) of the RF signal when the particle beam is present, where the current can be calculated from the absolute voltage (V) measured by signal analyzer 106 and the shunt impedance (Z), based on the Ohm's law (I=V/Z).

RF detector(s) 102 as shown in FIG. 1 includes N RF detectors. i.e., 102-1, RF detector 102-2, . . . , RF detector 102-N, where N can be any number equal to or greater than 1. A single RF detector 102 can allow for detection of the intensity of the particle beam in one location and along one direction in the radiation enclosure. Multiple RF detectors 102 can allow for detection of the intensity of the particle beam in multiple locations and/or along multiple directions in the radiation enclosure, thereby allowing for monitoring a transverse intensity profile of the particle beam. In one embodiment, multiple RF detectors 102 include a first group of RF detectors positioned for monitoring the transverse intensity profile of the particle beam in a first direction and second group of RF detectors positioned for monitoring the intensity profile of the particle beam in a second direction. The first direction can be perpendicular to the second direction. For example, the first direction can be the horizontal direction, and the second direction can be the vertical direction.

RF cavity 104 and waveguide(s) 103 of each of RF detector(s) 102 can be made of a radiation-resistant metal and filled with an ionization gas having a permittivity measurable as an indicator of the intensity of the particle beam. In one embodiment, the radiation-resistant metal includes aluminum, which is known to be robust for radiation. In one embodiment, the ionization gas includes nitrogen or helium gas. In one embodiment, a small amount of electronegative gas is added as a dopant in the ionization gas to control the dynamics of its plasma formed in the radiation enclosure.

Signal analyzer 106 can measure a shunt impedance of RF cavity 104 of each of RF detector(s) 102 and self-calibrate measurements for that RF detector using the shunt impedance measured without the presence of the particle beam. Signal analyzer 106 can determine an amplitude change and/or a phase change using the forward and returning RF signals received from each of RF detector(s) 102. The amplitude change is a difference between amplitudes of the received forward and returning RF signals. The phase change is a difference between phases of the received forward and returning RF signals. The amplitude change and/or phase change are indicative of an intensity of the one or more absolute intensities of the particle beam.

In one embodiment, waveguide(s) 103 include an input waveguide for transmitting the forward RF signal to RF cavity 104 through an input port of RF cavity 104 and an output waveguide for transmitting the returning RF signal from RF cavity 104 through an output port of RF cavity 104. The returning RF signal is an output RF signal produced by passing the forward RF signal through RF cavity 104. In another embodiment, waveguide(s) 103 include a single input-output waveguide for transmitting the forward RF signal to the gas-filled RF cavity and transmitting the returning RF signal from the gas-filled RF cavity through a single port of RF cavity 104. The returning RF signal is a reflected RF signal produced by reflecting a portion of the forward RF signal back from the RF cavity 104 through the single port. In various embodiments, waveguide(s) 103 can include the input waveguide and/or the output waveguide, and the returning RF signal to be analyzed using signal analyzer 106 can include the reflected RF signal and/or the output RF signal.

In various embodiments, signal analyzer 106 can measure the power of the forward RF signal and the power of the returning RF signal in real time. One or more absolute intensities of the particle beam can be determined using the difference between the power of the forward RF signal and the power of the returning RF signal determined for each of RF detectors 102 and information including the composition (and hence properties) of the ionization gas and pressure of the ionization gas in RF cavity 104 and waveguide(s) 103 of each of RF detectors 102. The composition and pressure of the gas can be controlled using a gas system coupled to RF detector(s) 102 during measurements.

Figure 2:
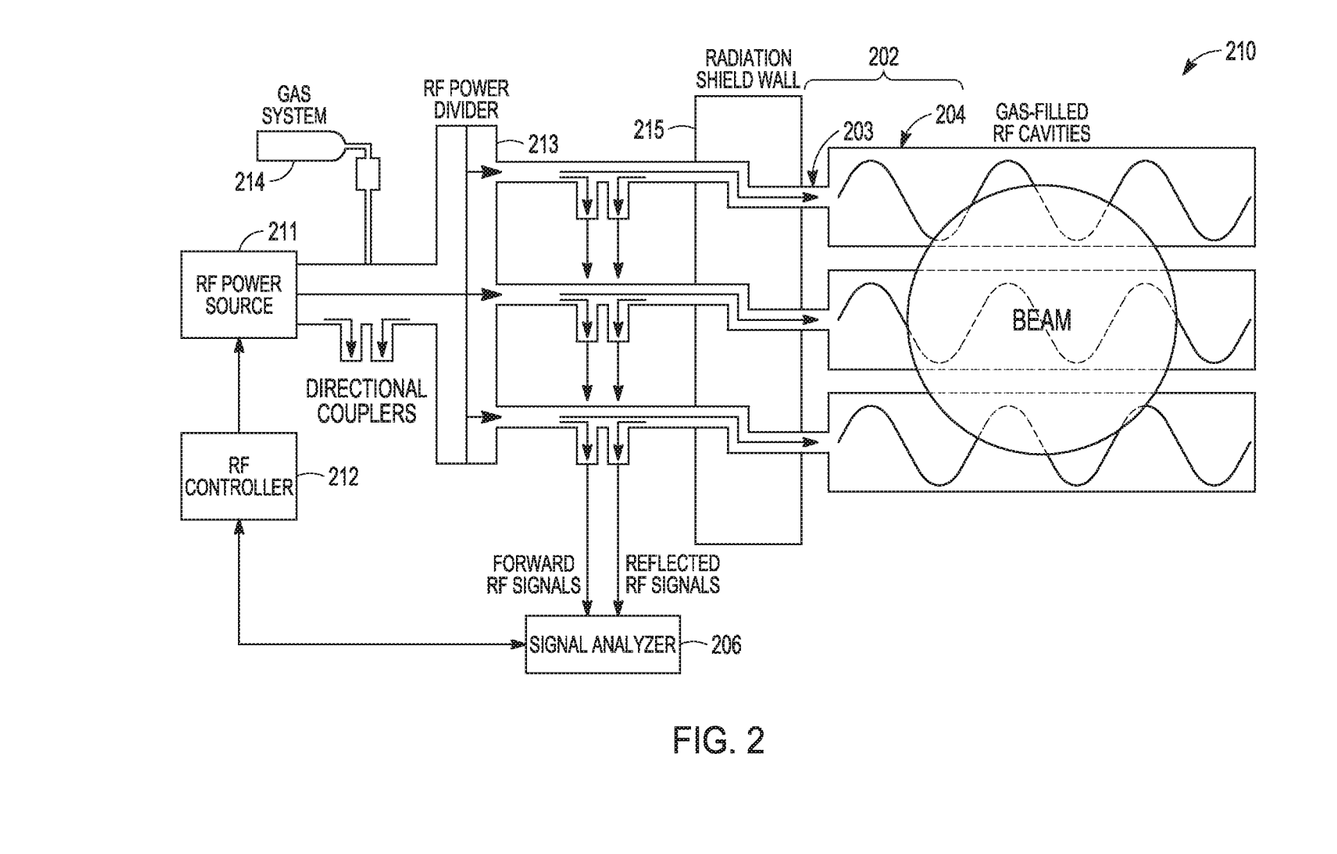
FIG. 2 illustrates an embodiment of a system for monitoring intensity profile of a particle beam inside a radiation enclosure using an RF beam intensity detector such as the RF beam intensity detector of FIG. 1.

FIG. 2 illustrates an embodiment of a system 210 for monitoring intensity profile of a particle beam inside a radiation enclosure using an RF beam intensity detector such as detector 100. System 210 includes multiple RF detectors 202, which can represent an example of RF detectors 102. Each of RF detectors 202 includes a waveguide 203, which can represent an example of waveguide 103, and an RF cavity 204, which can represent an example of RF cavity 104. While 3 RF detectors are shown in FIG. 2 as an illustrative example, RF detectors 202 can include any number of the RF detectors determined to provide a desirable resolution in monitoring the intensity profile of a particle beam. A radiation shield wall 215 represents the wall of the radiation enclosure. In FIG. 2, only RF cavities 204 and portions of waveguides 203 are within the radiation enclosure (i.e., on the right side of radiation shield wall 215 as illustrated). All the other elements of system 210 are placed outside the radiation enclosure (i.e., on the left side of radiation shield wall 215 as illustrated).

System 210 can further include an RF power source 211, an RF controller 212, an RF divider 213, a gas system 214, and a signal analyzer 206. RF power source 211 can generate an RF signal. RF controller 212 can control the generation of the RF signal including its intensity. RF divider 213 cam divide the RF signal generated by RF power source 211 into forward RF signals each fed into one of RF detectors 202. Gas system 214 can fill waveguides 203 and RF cavities 204 with the ionization gas and control the composition, flow, and pressure of the ionization gas.

Signal analyzer 206 can represent an example of signal analyzer 106. In the illustrated embodiment, signal analyzer 206 can receive both the forward RF signals and returning RF signals from waveguides 203 through directional couplers. The returning RF signals are reflected RF signals each being a portion of the forward RF signal reflected by one of RF cavities 204 and returned through the waveguide coupled to that RF cavity. Signal analyzer 206 can be used to monitor the intensity profile of the particle beam by analyzing the forward and reflected (returning) RF signals received from each of RF detectors 202. RF controller 212 can adjust the intensity of the RF signal for a suitable power level facilitating the monitoring by signal analyzer 206.

An example of a system in which the present subject matter can be applied is discussed in Yonehara et al., "Gas Filled RF Resonator Hadron Beam Monitor for Intense Neutrino Beam Experiments". Proceedings of IPAC2016. Busan, Korea. pp. 2733-2735 (2016), which is herein incorporated by reference in its entirety. In various embodiments, the present subject matter provides such a system with a self-calibration that can be performed with presence of a particle beam and allow for determination of absolute intensities of the particle beam. This can be done, for example, by using signal analyzer 206 to determine a shunt impedance of each of RF cavities 204 and self-calibrate using the shunt impedances.

Figure 3:
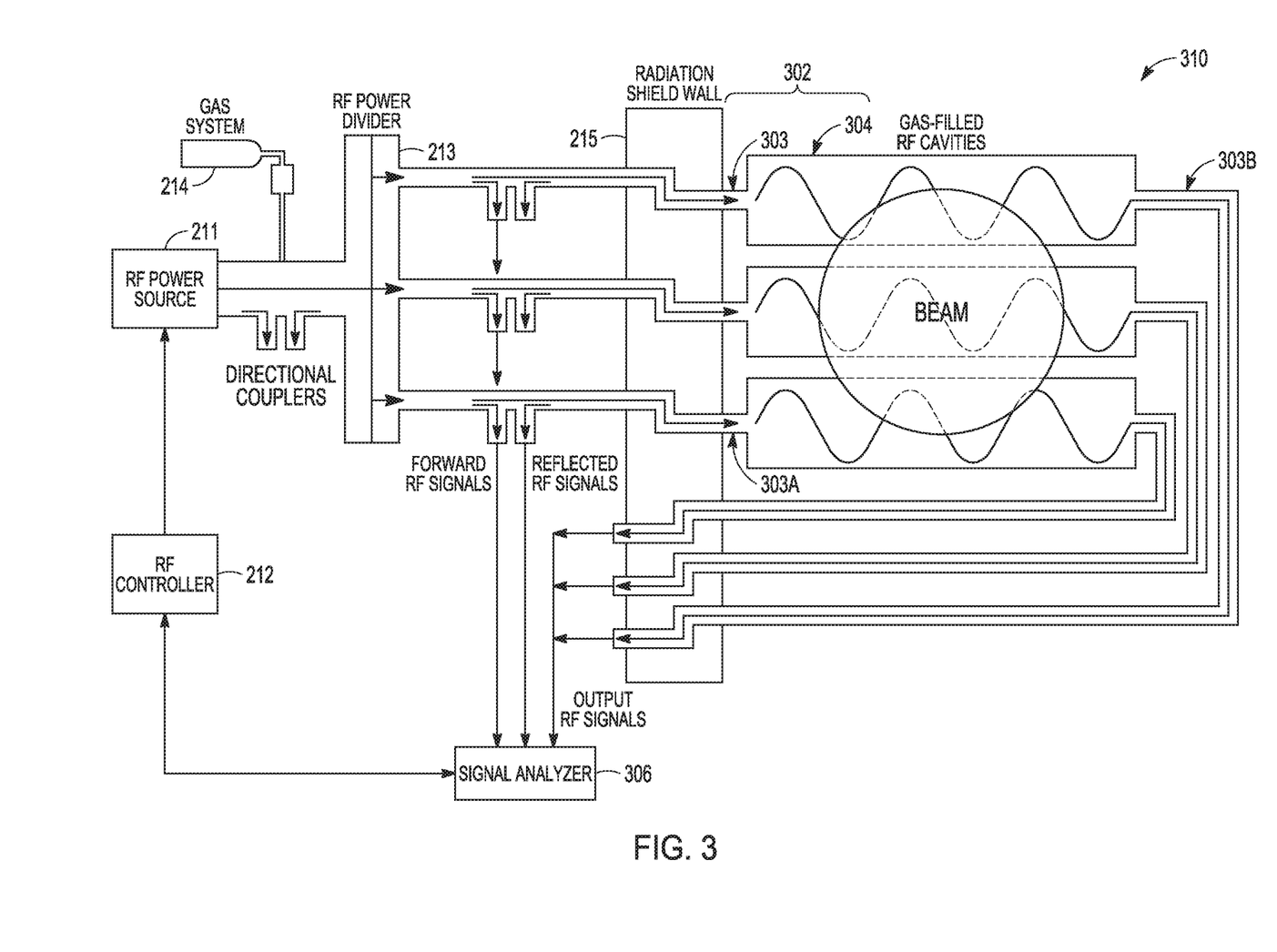
FIG. 3 illustrates another embodiment of a system for monitoring intensity profile of a particle beam inside a radiation enclosure using an RF beam intensity detector such as the RF beam intensity detector of FIG. 1.

FIG. 3 illustrates another embodiment of a system 310 for monitoring intensity profile of a particle beam inside a radiation enclosure using an RF beam intensity detector such as detector 100. System 310 includes multiple RF detectors 302, which can represent another example of RF detectors 102. Each of RF detectors 302 includes a waveguide 303, which can represent another example of waveguide 103, and an RF cavity 304, which can represent an example of RF cavity 104. While 3 RF detectors are shown in FIG. 3 as an illustrative example, RF detectors 302 can include any number of the RF detectors determined to provide a desirable resolution in monitoring the intensity profile of a particle beam. System 310 can be identical to system 210 except for RF detectors 302 and signal analyzer 306. In various embodiments, system 310 includes additional measurement capabilities not available from system 210, and can be configured to be used as system 210 (i.e., not using the additional measurement capabilities).

Waveguides 303 include input waveguides 303A each for transmitting the forward RF signal to one of the RF cavities 304 through an input port of that RF cavity and respective output waveguides 303B for transmitting an output RF signal from the one of the RF cavities 304 through an output port of that RF cavity. The output RF signals are each an output RF signal produced by passing the forward RF signal through one of RF cavities 304. Thus, in addition to the forward and reflected RF signals received by system analyzer 206, system analyzer 306 can receive and analyze the forward, reflected, and output RF signal for each of RF detector 302.

Signal analyzer 306 can represent another example of signal analyzer 106. In the illustrated embodiment, signal analyzer 306 can receive both the forward RF signals and reflected RF signals from waveguides 303A through directional couplers and can receive the output RF signals through waveguides 303B. Thus, signal analyzer 306 can be used to monitor the intensity profile of the particle beam by analyzing the forward and returning RF signals received from each of RF detectors 302, with the returning RF signals including the reflected and/or output RF signals. RF controller 212 can adjust the intensity of the RF signal for a suitable power level facilitating the monitoring by signal analyzer 306.

In various embodiments, the present subject matter provides a beam profile monitoring system such as system 210 or 310 with radiation-robust beam profile monitoring in which the only things in the radiation field of the beam are radiation-resistant metal and radiation-resistant gas. Study has shown that such a system can be simple and very robust in high-radiation environments. Charged particles passing through each RF cavity in the system produce ionized plasma, which changes the permittivity of the gas and the resonant frequency of the RF cavity. RF techniques for measuring the change in quality factor (Q) and frequency (f) as a function of time can be used to determine the change in permittivity of the gas and the corresponding beam intensity in each RF cavity in system. Beam intensity sensitivity is adjustable by varying gas pressure and amplitude of the RF signal. The beam profile can be reconstructed from the signals from individual RF cavities built into the beam profile monitoring system.

In one example, a beam profiling monitoring system similar to system 210 is analyzed. This system includes multiple metallic microwave cavities and waveguides. The forward and the reflected RF signals from each cavity are picked up with a directional coupler to measure the power lost in the cavity. The reflected RF signal is removed by a circulator and load (not shown in FIG. 2), which are located between the RF source and the directional coupler to prevent cross-talk. An RF capacitive or inductive pick-up inside each cavity (not shown in FIG. 2) provides a third signal for the analysis. These signals are fed into a signal analyzer located behind the radiation shield wall to determine the change in quality factor and frequency that are generated by the change in gas permittivity induced by the beam. Aluminum is used to make the cavity wall and the coaxial cable since it is robust for radiation. Nitrogen or helium gas is used for the ionization gas. A small amount of electronegative gas is added as a dopant in the gas to control the plasma dynamics. This system is so simple that it promises to be radiation robust in comparison with ionization chambers.

Each RF cavity has a width of 30 mm. A horizontal profile of the beam is defined using 12 RF cavities, and a vertical profile of the beam is defined using another 12 RF cavities. The position resolution of the beam center is better than 0.5 mm, which allows the angle of the primary proton beam to be determined to within 2.5 μrad. The RF cavity size determines the resonant frequency, which is 5 GHz. Because the plasma permittivity is given by the abundance of plasma particles in the neutral gas, the gap in the beam direction is a free parameter, and is 1 cm in the analysis.

Varying the gas pressure is the primary tuning knob to control the plasma dynamics. The pressurized gas quickly thermalizes ionization electrons. The design pressure is 1 atm to simplify the analysis. Gas is sent to the RF cavity through the waveguide. Varying the RF gradient is another tuning knob to control the plasma dynamics. The range of possible RF gradient is 0.001-1 MV/m. The maximum gradient in the gas-filled RF cavity is limited by the electric breakdown of the gas.

The permittivity of beam-induced plasma is given by:

$$\frac{\varepsilon}{\varepsilon_0} = 1 + \frac{n_e e^2}{\varepsilon_0 m(\omega_{RF}^2 + v^2)}\left(1 + i\frac{v}{\omega_{RF}}\right), \quad (1)$$

where m, $n_e$, v and $\omega_{RF}$ are electron mass, the total number of electrons, the collision frequency with gas and the driving frequency of RF, respectively. Yonehara et al, "New Hadron Monitor by Using a Gas-Filled RF Resonator", Proceedings of IPAC 2015, Richmond, Va. U.S.A. (2015). Equation (1) can be separated into real and imaginary components, which are proportional to the number of ionization electrons. The real component is the dielectric constant, which changes the resonant frequency of the cavity. The imaginary component represents the RF energy consumption, corresponding to losses due to electrons oscillating due to the RF field in a resistive medium. Consequently, the electron kinetic energy, which is gained from the RF field, is transferred into heating of the gas like $I^2R/2$.

The imaginary component can be measured as the energy consumption rate per single ion pair as a function of the RF amplitude and the gas pressure. The energy consumption rate can be used to estimate the RF power loading by the beam-induced plasma in any kind of gas-filled RF cavity if the plasma and electromagnetic field distributions in the RF cavity are known.

Equation (1) shows that lower RF gradient is preferred for larger frequency shift to minimize the collision frequency. The largest frequency shift is achieved when the electron temperature equals the gas temperature. The real component changes the resonant frequency as $f \propto \varepsilon^{-1/2}$. The following relation is derived:

$$\frac{df}{f} = -\frac{1}{2} d\varepsilon/\varepsilon.$$

The plasma population equation to extract the ion production rate in the RF cavity $\dot{n}$ by the incident particles is $$\dot{n}_e = \frac{dn_e}{dt} + \beta n_e n_{ion} + \gamma n_e, \quad (2)$$

where β is the recombination rate, γ is the ion pair loss rate due to diffusion and absorption at the conductor wall and $n_{ion}$ is the number of ions. In pure $N_2$, the number of electrons is the same as the number of ions. For our RF parameters, β is $10^{-7}$ cm$^3$/s, while y$^{-1}$ is $10^{-3}$ second.

Doping a small amount of electronegative in the gas permits measurement of the time domain beam profile. Such a dopant causes electrons to be immediately captured by the electronegative atoms or molecules. Consequently, each captured electron effectively gains the mass of the electronegative atom or molecule, and its mobility becomes significantly lower. A term equal to τn is added in the right-hand side of Equation (2) when the dopant is added. Oxygen ($O_2$) is the baseline candidate dopant, for which r=$10^{-9}$ s is used in this analysis.

The energy consumption rate by the plasma, ΔP represents in the equivalent LC circuit equation, $$\Delta P = \frac{V(t)[V_0 - V(t)]}{R} - CV(t)\frac{dV(t)}{dt}, \quad (3)$$

where C and R are the capacitance and the shunt impedance of the RF cavity. V(t) is the time domain electric potential in the RF cavity, and $V_0$=V(0). The first term is the source term, i.e., the RF cavity voltage is restored by a RF power source or by an adjacent coupled-RF cell, while the second term is the time varying stored energy in the RF cavity. Equation (3) suggests that the sensitivity improves with a higher capacitance RF cavity.

In summary, the numerical result of the analysis indicates that the RF cavity will be useful to measure the beam profile with plasma sensitivity of $10^8$ to $10^{14}$ ion pairs in the RF cavity.

A thin waveguide is preferred to reduce geometry constraints in the system. However, the excited RF gradient in the waveguide is larger in a thinner waveguide. The electric field in the waveguide is estimated b using the formula:

$$E = \sqrt{\frac{1.51P}{4ab\sqrt{1-\left(\frac{\lambda}{\lambda_c}\right)^2}}}, \quad (4)$$

where P is the RF power propagating in the waveguide, a and b are the vertical and horizontal length of the waveguide, and $\lambda$ and $\lambda_c$ are the propagation wavelength and the critical wavelength, respectively. The estimated maximum RF gradient in the standard waveguide is 100 V/m or less in one example. In this case, the electron temperature is the same as the gas temperature so that the RF energy consumption at the maximum RF gradient in the waveguide is $dw \sim evE/f \sim 1.6 \times 10^{-19} \cdot 10^5$ [m/s] $\cdot 100$ [V/m]$/10^{10}$ [Hz] $\sim 10^{-22}$ J/RF cycle. This is five orders of magnitude lower than the energy consumption in the RF cavity. However, the total volume of the waveguide is several orders of magnitude larger than the RF cavity, so the total energy consumption in the waveguide may not be negligible.

Figure 4:
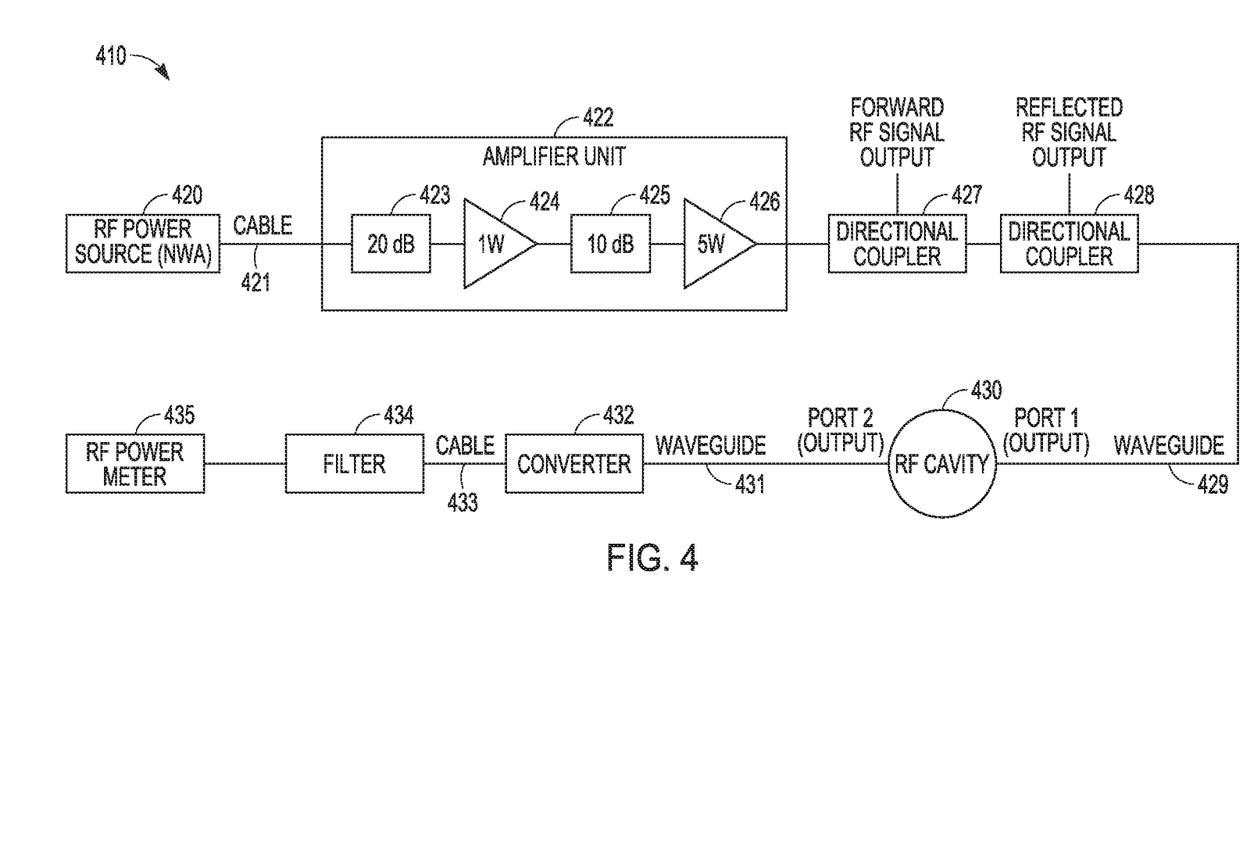
FIG. 4 illustrates an embodiment of a system including an electronic circuit for use with an RF detector to detect beam intensity, such an RF detector of FIG. 3.

FIG. 4 illustrates an embodiment of a system 410 including an electronic circuit for use with an RF detector to monitor beam intensity, such as one of RF detector 302. While the illustrated embodiment uses one RF detector for simplicity of discussion, the concept being illustrated is readily applicable to a beam profile monitoring system with multiple RF cavities, such as system 210 or 310, as those skilled in the art would understand upon reading this document.

In FIG. 4, system 410 is shown as a block diagram that also shows the electronic circuit that is coupled to the RF detector including an RF cavity 430 and waveguides 429 and 431. A prototype of system 410, including a 2.5 GHz RF detector and the electronics to read out the RF signals to measure the beam intensity, was built and tested, as discussed below.

The excited RF field in a gas-filled RF cavity is changed by beam-induced gas plasma in the RF cavity. The process of these RF changes can be interpreted as a gas permittivity shift due to plasma formation in the RF cavity. The permittivity consists of real and imaginary parts. The real part changes the resonant frequency of RF cavity while the imaginary part changes the quality factor of RF cavity. The size of the shift is proportional to the amount of plasma and hence proportional to the beam intensity. The estimated frequency shift is comparable with other shifts due to thermal expansion of the RF cavity. Therefore, change in the quality factor is observed in the prototype of system 410.

In the illustrated embodiment, an RF power source 420, for which a network analyzer (NWA) was used for the prototype, generates RF power in the range from 0 to 20 dBm. The RF signal is sent through a long 0.5-inch heliax cable 421 to an amplifier unit 422. Amplifier unit 422 compensates the insertion loss of cable 421 and includes two amplifiers 424 (1 W) and 426 (5 W) and two attenuators 423 (20 dB) and 425 (10 dB), which are used to filter out RF noise and to minimize the non-linear behavior of a single amplifier. The amplified RF signal then goes through two directional couplers 427 and 428 for measuring the forward and reflected RF signals. The RF signal (i.e., the forward RF signal) is then fed by an input waveguide 429 to port 1 (an input coupler) of RF cavity 430 (a 2.45 GHz gas filled RF cavity) that is used to measure the charged-particle flux. The output RF signal is taken from port 2 (an output coupler) of RF cavity 430. In order to tune the quality factor (Q) of RF cavity 430 (i.e., to have the correct loaded Q), port 2 (output coupler) is slightly under-coupled. The output RF signal is sent from port 2 through an output waveguide 432 and sent to a long heliax cable 433 through a converter 432, and is then and filtered using a filter 434 (1.6 dB). The filtered output RF signal is fed into a real-time RF power meter 435. The power lost in RF cavity 430 is determined by comparing the power sent by RF power source 420 to the power received by RF power meter 435. This power loss and the knowledge of the gas composition and pressure are all that are needed to determine the intensity of the beam passing through RF cavity 430.

A gas system (not shown in FIG. 4) feeds the input waveguide 429, output waveguide 431, and RF cavity 430 with the gas. The precise control of the composition, pressure, and flow rates of the gas (e.g., nitrogen, helium, or dry air as tested with the prototype) are essential for long term stability and reliability.

The prototype of system 410 was demonstrated to be adequate for the measurements described below and proves that a relatively simple electronic circuit can be used for the radiation-robust gas-filled radio-frequency beam-detector. Thus, the simple designs of the RF detector and the associated electronics are aspects of what will be an extremely reliable and relatively cost effective beam intensity monitor, and, when configured as arrays, beam profile monitors.

Input waveguide 429, output waveguide 431, and RF cavity 430 are made of radiation-resistant metal (e.g., aluminum) and filled with gas (e.g., nitrogen) and are the only parts that are expected to be in the high radiation field generated by the high intensity particle beam. This feature of having only gas and metal in the beam radiation field and all electronic parts out of the radiation field is the basis of the radiation robustness of the present subject matter.

Figure 5:
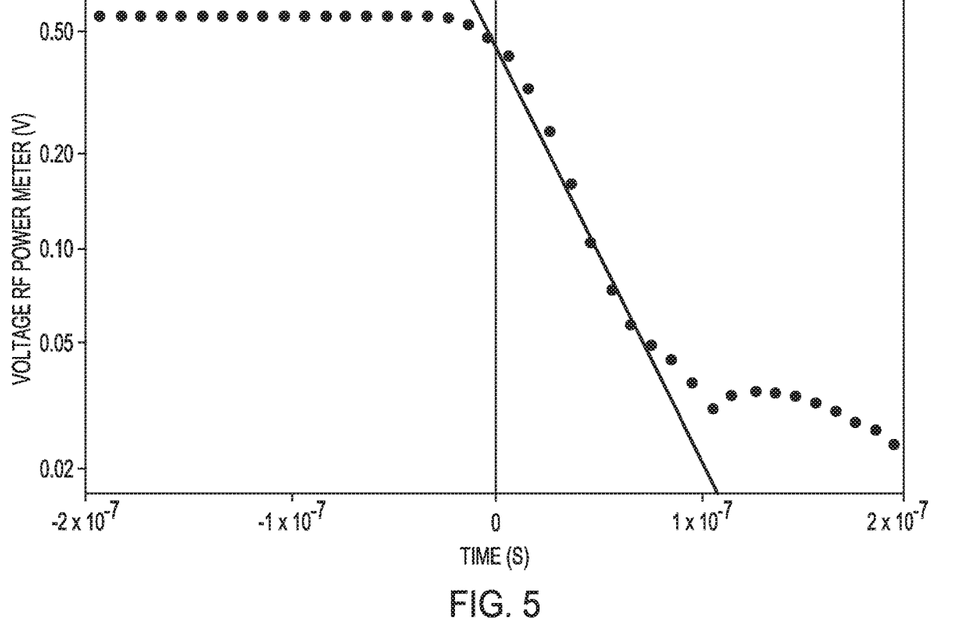
FIG. 5 illustrates an example of observed decay time in an RF detector without beam, resulting from an experiment using a prototype of the electronic circuit of FIG. 4.

FIG. 5 illustrates an example of decay time in an RF detector without beam, observed with the prototype of system 410. It shows the observed RF signal amplitude in the RF detector when RF power source 420 is turned off. The quality factor is estimated by measuring the decay time of the RF signal.

The observed decay time constant is $\tau=1.65 \times 10^{-8}$ s. The driving frequency is $v_0=2.385$ GHz. Thus, the quality factor is $Q=\tau \cdot 2\pi \cdot v_0=247$. The quality factor can also be measured from the spectrum of the RF detector.

Figure 6:
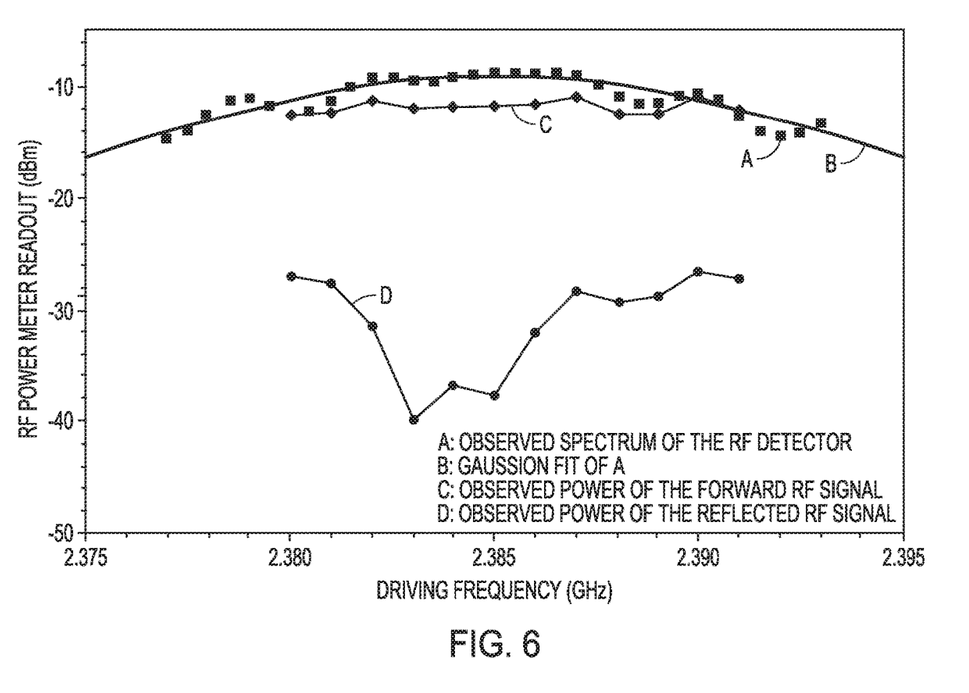
FIG. 6 illustrates an example of observed spectrum of the RF detector and observed power of forward and reflected RF signals, resulting from the experiment using the prototype of the electronic circuit of FIG. 4.

FIG. 6 illustrates an example of the spectrum of the RF detector and power of forward and reflected RF signals, observed with the prototype of system 410. The frequency width of the spectrum is 10 MHz, and thus the quality factor is $Q=\Delta v/v_0=239$.

Figure 7:
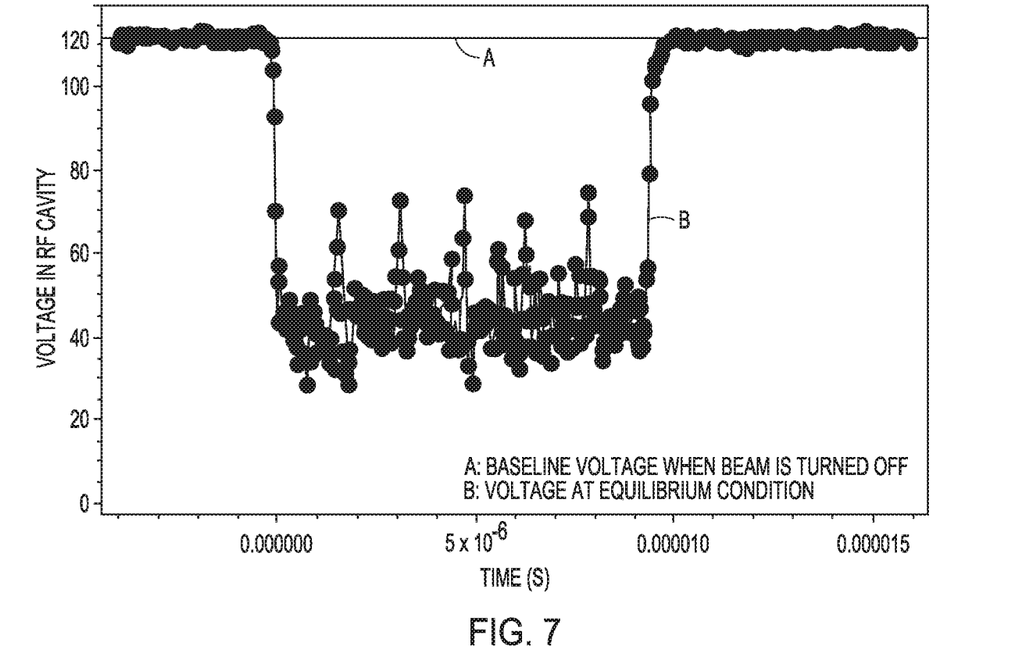
FIG. 7 illustrates an example of observed RF signal amplitudes in the RF detector without and with beam loading, resulting from the experiment using the prototype of the electronic circuit of FIG. 4.

FIG. 7 illustrates an example of RF signal amplitudes in the RF detector without and with beam loading, observed with the prototype of system 410. The amplitude is 112 V when the beam is turned off. When the RF detector detects the beam, the amplitude drops and reaches an equilibrium amplitude. The amplitude drop is caused by the quality factor shift due to the beam-induced plasma. The observed equilibrium amplitude is 40 V. The time resolution of real time RF power meter 435 is 40 ns, which is sufficient to detect the amplitude drop. The test beam has a six-batch structure. The electronics also shows six batches. The equilibrium amplitude also indicates the average beam intensity in the RF detector.

Figure 8:
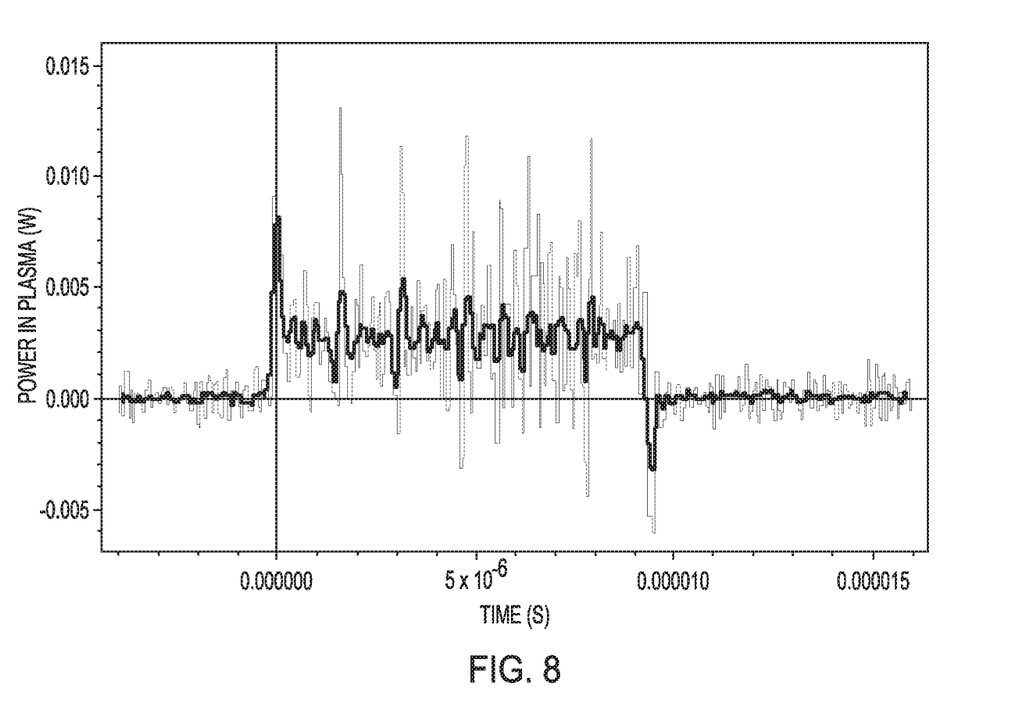
FIG. 8 illustrates an example of RF power dissipation in the beam-induced plasma estimated using RF signal amplitude measured from the experiment using the prototype of the electronic circuit of FIG. 4.

FIG. 8 illustrates an example of RF power dissipation in the beam-induced plasma estimated using RF signal amplitude measured with the prototype of system 410. The number of ionized particles in the RF detector can be estimated from the power dissipation.

The prototype of system 410 results from development of a radiation hard gas-filled RF detector for measuring beam intensities in severe radiation environments for future beam facilities. The prototype provided for testing of the read-out electronics for the RF detector. It reads the RF signal within 40 ns and can be used to calibrate measurements of the RF signal from the RF detector. The observed equilibrium amplitude showed linear correlation with the beam intensity.

A multi-channel RF detector has been developed to measure the transverse beam profile. The read-out electronics as illustrated in FIG. 4 is suitable for the beam profile monitor because it is simple. Software has been developed to reconstruct the beam profile from the signals of a multiple-channel RF detector.

System 410 as illustrated in FIG. 4 will be similar to what is needed for a beam profile monitor, which can include 3 to 5 (or more) detectors (each including input waveguide 429, output waveform 431, and RF cavity 430), side by side, to measure a horizontal (x) profile and another 3 to 5 (or more) detectors rotated 90 degrees to measure the vertical (y) profile. These detectors can be self-calibrated to get absolute beam intensities from each detector. That is, the shunt impedance for each detector can be measured without the beam. From Ohm's law, the absolute beam intensity (current) in each detector can be derived from the measured voltage induced by the beam in each detector divided by its shunt impedance.

Figure 9:
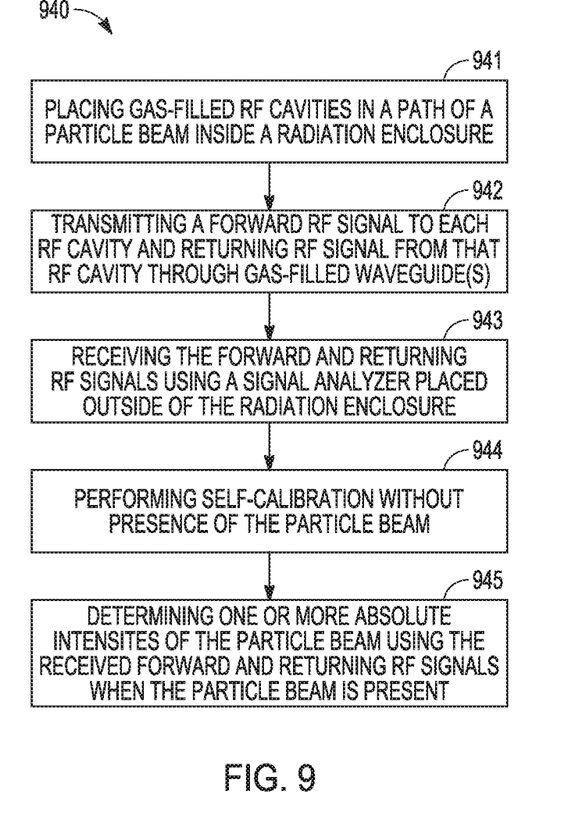
FIG. 9 illustrates an embodiment of a method for detecting intensity of a particle beam inside a radiation enclosure.

FIG. 9 illustrates an embodiment of a method 940 for detecting intensity of a particle beam inside a radiation enclosure. In various embodiments, method 940 can be performed using system 210, 310, or 410. Method 940 was developed and experimentally verified with the prototype of system 410. To perform method 940, one or more RF detectors each including a gas-filled RF cavity and one or more gas-filled waveguides coupled to the RF cavity are provided.

At 941, the one or more RF cavities are placed in a path of the particle beam inside the radiation enclosure. In one embodiment, multiple RF cavities are placed in the path of the particle beam for monitoring a transverse intensity profile of the particle beam multiple RF cavities in the path of the particle beam for monitoring a transverse intensity profile of the particle beam. This can include, for example, placing a first group of the multiple gas-filled RF cavities for monitoring a horizontal intensity profile of the particle beam and placing a second group of the multiple RF gas-filled cavities for monitoring a vertical intensity profile of the particle beam.

At 942, a forward RF signal is transmitted to each RF cavity of the one or more RF cavities, and a returning RF signal is transmitted from that RF cavity, through the one or more gas-filled waveguides. In one embodiment, a single waveguide is used for transmitting the forward RF signal to each RF cavity and the returning RF signal from that RF cavity. The returning RF signal is a portion of the forward RF signal reflected by the RF cavity. In another embodiment, the forward RF signal is transmitted to each RF cavity through an input waveguide, and the returning RF signal is transmitted from that RF cavity through an output waveguide. The returning RF signal is a portion of the forward RF signal passing through the each RF cavity.

At 943, the forward and returning RF signals are received by a signal analyzer placed outside the radiation enclosure and coupled to the one or more waveguides.

At 944, a self-calibration is performed for each RF cavity of the one or more RF cavities without presence of the particle beam. The self-calibration allows for determination of one or more absolute intensities of the particle beam using the received forward and returning RF signals. A shunt impedance of each RF cavity can be measured without the presence of the particle beam, and the self-calibration of each RF cavity can be performed using the shunt impedance measured for that RF cavity.

At 945, the one or more absolute intensities of the particle beam is determined using the received forward and returning RF signals when the particle beam is present after the self-calibration. The one or more absolute intensities of the particle beam can be determined by determining an amplitude change and/or a phase change using the forward and returning RF signals received from each RF cavity of the one or more RF cavities. The amplitude change is the difference between amplitudes of the received forward and returning RF signals, and is indicative of an intensity of the one or more absolute intensities of the particle beam. The phase change is the difference between phases of the received forward and returning RF signals, and is indicative of an intensity of the one or more absolute intensities of the particle beam.

In various embodiments, to perform method 940, a gas is fed to each RF cavity and the one or more waveguides coupled to that RF cavity, with the composition of the gas and the pressure of the gas being controlled. A power loss in each RF cavity can be determined by calculating the difference between the power of the forward RF signal and the power of the returning RF signal. The absolute intensity of the particle beam at each RF cavity can be determined using the composition of the gas, the pressure of the gas, and the power loss in that RF cavity. In various embodiment, the composition of the gas, the pressure of the gas, and the power loss in each RF cavity are all that are needed for determining the absolute intensity of the particle beam at that RF cavity.

It is to be understood that the above detailed description is intended to be illustrative, and not restrictive. Other embodiments will be apparent to those of skill in the art upon reading and understanding the above description.

What is claimed is:

1. An apparatus for monitoring intensity of a particle beam inside a radiation enclosure, the apparatus comprising:
    one or more radio-frequency (RF) detectors each including:
        a gas-filled RF cavity configured to be placed inside the radiation enclosure; and
        one or more gas-filled waveguides coupled to the gas-filled RF cavity for transmitting a forward RF signal to the gas-filled RF cavity and a returning RF signal from the gas-filled RF cavity; and
    a signal analyzer configured to be placed outside of the radiation enclosure and coupled to the one or more gas-filled waveguides of each RF detector of the one or more RF detectors to receive the forward and returning RF signals, to self-calibrate without presence of the particle beam for determining one or more absolute intensities of the particle beam using the received forward and returning RF signals, and to determine the one or more absolute intensities of the particle beam using the received forward and returning RF signals when the particle beam is present after the self-calibration.

2. The apparatus of claim 1, wherein the one or more RF detectors comprise multiple RF detectors configured to be positioned for monitoring a transverse intensity profile of the particle beam.

3. The apparatus of claim 2, wherein the multiple RF detectors comprise first RF detectors positioned for monitoring the transverse intensity profile of the particle beam in a first direction and second RF detectors positioned for monitoring the intensity profile of the particle beam in a second direction, the first direction perpendicular to the second direction.

4. The apparatus of claim 1, wherein the signal analyzer is configured to measure a shunt impedance of each RF detector of the one or more RF detectors and to self-calibrate using the shunt impedance measured without the presence of the particle beam.

5. The apparatus of claim 1, wherein the gas-filled RF cavity and the one or more gas-filled waveguides of each RF detector of the one or more RF detectors are made of a radiation-resistant metal and filled with a gas having a permittivity measurable as an indicator of the intensity of the particle beam.

6. The apparatus of claim 5, wherein the gas-filled RF cavity and the one or more gas-filled waveguides of each RF detector of the one or more RF detectors are made of aluminum.

7. The apparatus of claim 6, wherein the gas-filled RF cavity and the one or more gas-filled waveguides of each RF detector of the one or more RF detectors are filled with a gas including nitrogen and an electronegative gas added as a dopant.

8. The apparatus of claim 5, wherein the signal analyzer is configured to determine at least one of an amplitude change or a phase change using the forward and returning RF signals received from each RF detector of the one or more RF detectors, the amplitude change being a difference between amplitudes of the received forward and returning RF signals, the phase change being a difference between phases of the received forward and returning RF signals, the at least one of an amplitude change or a phase change indicative of an intensity of the one or more absolute intensities of the particle beam.

9. The apparatus of claim 5, wherein the one or more gas-filled waveguides comprise an input waveguide for transmitting the forward RF signal to the gas-filled RF cavity and an output waveguide for transmitting the returning RF signal from the gas-filled RF cavity.

10. The apparatus of claim 5, wherein the one or more gas-filled waveguides comprise a single input-output waveguide for transmitting the forward RF signal to the gas-filled RF cavity and transmitting the returning RF signal from the gas-filled RF cavity.

11. A method for monitoring intensity of a particle beam inside a radiation enclosure, the method comprising:
placing one or more gas-filled radio-frequency (RF) cavities in a path of the particle beam inside the radiation enclosure;
transmitting a forward RF signal to each RF cavity of the one or more gas-filled RF cavities and a returning RF signal from that RF cavity through one or more gas-filled waveguides coupled to that RF cavity;
receiving the forward and returning RF signals using a signal analyzer placed outside the radiation enclosure and coupled to the one or more gas-filled waveguides coupled to each RF cavity of the one or more gas-filled RF cavities;
performing self-calibration for each RF cavity of the one or more gas-filled RF cavities without presence of the particle beam for determining one or more absolute intensities of the particle beam using the received forward and returning RF signals; and
determining the one or more absolute intensities of the particle beam using the received forward and returning RF signals when the particle beam is present after the self-calibration.

12. The method of claim 11, wherein placing the one or more gas-filled RF cavities in the path of the particle beam comprises placing multiple gas-filled RF cavities in the path of the particle beam for monitoring a transverse intensity profile of the particle beam.

13. The method of claim 12, wherein placing multiple gas-filled RF cavities in the path of the particle beam for monitoring the transverse intensity profile of the particle beam comprises:
placing a first group of the multiple gas-filled RF cavities for monitoring a horizontal intensity profile of the particle beam; and
placing a second group of the multiple gas-filled RF cavities for monitoring a vertical intensity profile of the particle beam.

14. The method of claim 11, wherein performing the self-calibration for each RF cavity comprises:
measuring a shunt impedance of the each RF cavity without the presence of the particle beam; and
performing the self-calibration for the each RF cavity using the measured shunt impedance.

15. The method of claim 14, wherein determining the one or more absolute intensities of the particle beam comprises determining an amplitude change using the forward and returning RF signals received from each RF cavity of the one or more gas-filled RF cavities, the amplitude change being a difference between amplitudes of the received forward and returning RF signals and being indicative of an intensity of the one or more absolute intensities of the particle beam.

16. The method of claim 14, wherein determining the one or more absolute intensities of the particle beam comprises determining a phase change using the forward and returning RF signals received from each RF cavity of the one or more gas-filled RF cavities, the phase change being a difference between phases of the received forward and returning RF signals and being indicative of an intensity of the one or more absolute intensities of the particle beam.

17. The method of claim 11, wherein transmitting the forward RF signal to the each RF cavity and the returning RF signal from that RF cavity comprises transmitting the forward RF signal to the each RF cavity and the returning RF signal from that RF cavity through a single waveguide coupled to that RF cavity, and the returning RF signal is a portion of the forward RF signal reflected by the each RF cavity.

18. The method of claim 11, wherein transmitting the forward RF signal to the each RF cavity and the returning RF signal from that RF cavity comprises:
transmitting the forward RF signal to that RF cavity through an input waveguide coupled to that RF cavity; and
transmitting the returning RF signal from that RF cavity through an output waveguide coupled to that RF cavity, and wherein the returning RF signal is a portion of the forward RF signal passing through the each RF cavity.

19. The method of claim 11, further comprising:
feeding a gas to each RF cavity of the one or more gas-filled RF cavities and the one or more gas-filled waveguides coupled to that RF cavity;
controlling a composition of the gas and a pressure of the gas;
measuring a power loss in the each RF cavity being a difference of a power of the forward RF signal transmitted to that RF cavity and a power of the returning RF signal transmitted from that RF cavity; and
determining the absolute intensity of the particle beam for the each RF cavity using the composition of the gas, the pressure of the gas, and the power loss in that RF cavity.

20. The method of claim 19, further comprising:
using a radiation-resistant metal to construct the one or more gas-filled RF cavities and the one or more gas-filled waveguides coupled to each RF cavity of the one or more gas-filled RF cavities; and
using a radiation-resistant gas as the gas fed to the each RF cavity and the one or more gas-filled waveguides coupled to that RF cavity.

\* \* \* \* \*

UNITED STATES PATENT AND TRADEMARK OFFICE
CERTIFICATE OF CORRECTION

| | | |
|---|---|---|
| PATENT NO. | : 11,525,931 B2 | |
| APPLICATION NO. | : 16/855125 | |
| DATED | : December 13, 2022 | |
| INVENTOR(S) | : Yonehara et al. | |

It is certified that error appears in the above-identified patent and that said Letters Patent is hereby corrected as shown below:

On the Title Page

On page 2, in Column 2, under "Other Publications", Line 28, delete "NuMl" and insert --NuMI-- therefor On page 2, in Column 2, under "Other Publications", Line 30, delete "NuMl" and insert --NuMI-- therefor Signed and Sealed this
Seventeenth Day of October, 2023

Katherine Kelly Vidal
*Director of the United States Patent and Trademark Office*